United States Patent
Liu et al.

(10) Patent No.: US 10,058,611 B2
(45) Date of Patent: Aug. 28, 2018

(54) USE OF α-(8-QUINOLINYLOXY) MONO-SUBSTITUTED PHTHALOCYANINE ZINC FOR TREATMENT OF PSORIASIS

(71) Applicant: BEIJING GUIQIANJIN MEDICAL SCIENCE AND TECHNOLOGY CO., LTD., Beijing (CN)

(72) Inventors: Hanqing Liu, Beijing (CN); Aiping Wang, Beijing (CN); Jinfeng Wei, Beijing (CN); Hongtao Jin, Beijing (CN); Qianaian Zhang, Beijing (CN); Ni Lin, Beijing (CN); Zhihuan Jiang, Beijing (CN); Xiaodan Yan, Beijing (CN); Ye Li, Beijing (CN); Jingyi Feng, Beijing (CN); Yingming Wang, Beijing (CN)

(73) Assignee: BEIJING GUIQIANJIN MEDICAL SCIENCE AND TECHNOLOGY CO., LTD. (CN)

( * ) Notice: Subject to any disclaimer, the term of this patent is extended or adjusted under 35 U.S.C. 154(b) by 0 days.

(21) Appl. No.: 15/508,023

(22) PCT Filed: Sep. 2, 2014

(86) PCT No.: PCT/CN2014/000819
§ 371 (c)(1),
(2) Date: Mar. 1, 2017

(87) PCT Pub. No.: WO2016/033705
PCT Pub. Date: Mar. 10, 2016

(65) Prior Publication Data
US 2017/0296662 A1 Oct. 19, 2017

(30) Foreign Application Priority Data
Sep. 1, 2014 (CN) .......................... 2014 1 043809

(51) Int. Cl.
A61K 41/00 (2006.01)
A61N 5/06 (2006.01)
A61N 5/067 (2006.01)

(52) U.S. Cl.
CPC .......... *A61K 41/0076* (2013.01); *A61N 5/062* (2013.01); *A61N 5/0616* (2013.01); *A61N 2005/067* (2013.01); *A61N 2005/0663* (2013.01)

(58) Field of Classification Search
CPC .. A61K 41/0076; A61N 5/0616; A61N 5/062; A61N 2005/0663; A61N 2005/067
See application file for complete search history.

(56) References Cited

U.S. PATENT DOCUMENTS 5,965,598 A * 10/1999 Roncucci ........... A61K 41/0071
514/183

FOREIGN PATENT DOCUMENTS

CN 101260110 A 9/2008

OTHER PUBLICATIONS

Xue et al (CN101260110A, published Sep. 10, 2008, Machine Translation) (Year: 2008).*

* cited by examiner

*Primary Examiner* — Kortney L Klinkel
*Assistant Examiner* — Ibrahim D Bori
(74) *Attorney, Agent, or Firm* — Morriss O'Bryant Compagni Cannon, PLLC

(57) ABSTRACT

The present invention relates to a use of alpha-(8-quinolinyloxy) mono-substituted phthalocyanine zinc for the treatment of psoriasis. The use is suitable for various type of psoriasis by utilizing photodynamic therapy. The photosensitizer is used to treat psoriasis by utilizing laser wave length of 670 nm, with high light sensitivity, fast photobleaching, short time needed in protection from light, and avoiding potential toxic and side-effect of photochemistry therapy by using ultraviolet irradiation. The preparation used in the use of α-(8-quinolinyloxy) mono-substituted phthalocyanine zinc for the treatment of psoriasis includes solution, cream, nanomicelle, microsphere etc, and mode of administration can be systemic or topical administration. The practicability of treating psoriasis by photodynamic therapy has been validated on cell and animal model. The use achieves perfect effect.

8 Claims, 4 Drawing Sheets

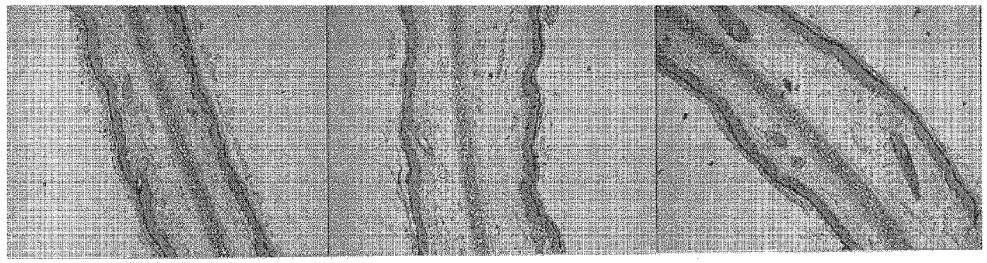
Figure 4A Blank control group
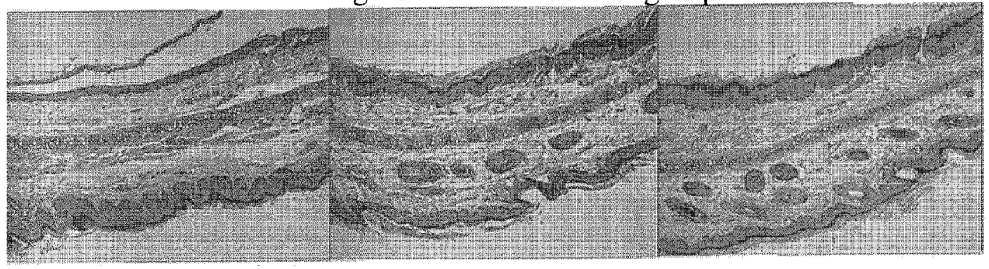
Figure 4B Model control group
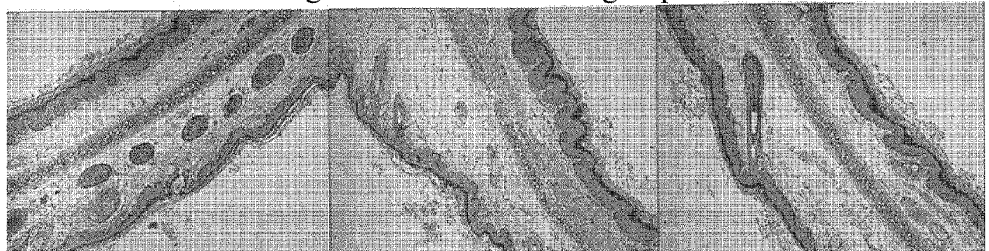
Figure 4C Irradiation without administration group
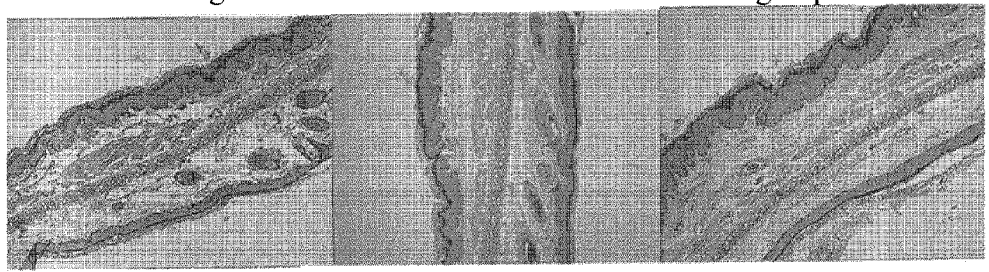
Figure 4D Administration without irradiation group
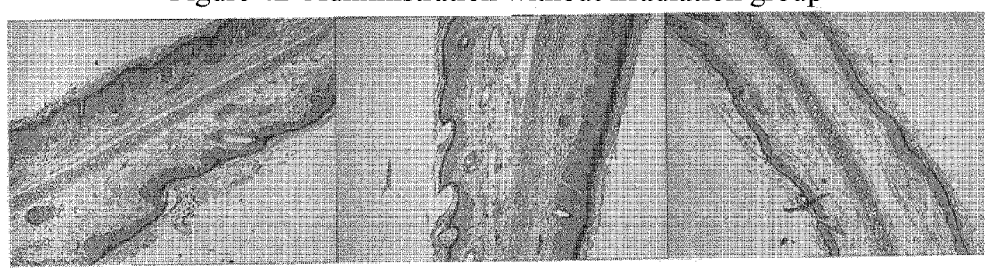
Figure 4E Injection administration group

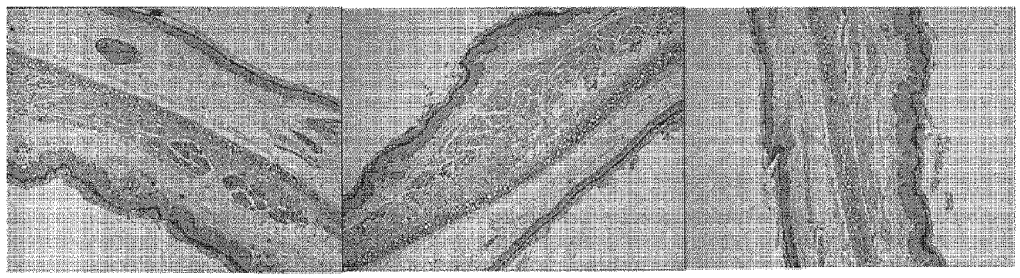
Figure 4F Topic administration group 1
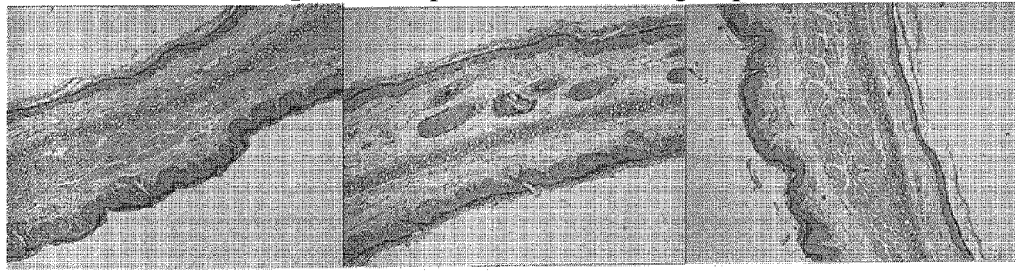
Figure 4G Topic administration group 2

USE OF α-(8-QUINOLINYLOXY) MONO-SUBSTITUTED PHTHALOCYANINE ZINC FOR TREATMENT OF PSORIASIS

CROSS-REFERENCE TO RELATED APPLICATIONS

This application is a national phase entry under 35 U.S.C. § 371 of PCT/CN2014/000819 filed on Sep. 2, 2014, which claims priority to Chinese Patent Application No. 201410438091.7 filed on Sep. 1, 2014, the entirety of each of which is incorporated by reference.

TECHNICAL FIELD

The present invention relates to use of a photodynamic therapy of α-(8-quinolinyloxy) mono-substituted phthalocyanine zinc for the treatment of psoriasis, which is suitable for the treatment of psoriasis cells, animal models and patients with various types of psoriasis.

BACKGROUND ART

Psoriasis is a chronic inflammatory skin disease characterized by hyperproliferative epidermis accompanied with parakeratosis and lymphocytic infiltration of the dermis; psoriasis is mainly manifested by erythemas and scales, and has complex pathogenesis and long disease course; it is easy to relapse and difficult to cure, severely affects the quality of life of patients. As compared with United States and Europe, the prevalence of psoriasis is lower but the absolute number of patients is greater and is increasing year by year in China. The objective of psoriasis treatment is to control the disease, delay the process of systematic development, alleviate symptoms such as erythemas, scales, topical thickening patches and the like, stabilize the disease condition, prevent recurrence, avoid side effects and improve the quality of life of patients and such treatment should follow regular, safe and individualized treatment principles. Currently, the therapeutic methods for psoriasis are mainly external drugs therapies and physical therapies. The external drugs include emollients, keratoplastics, keatolytics, corticosteroids, tretinoins, vitamin D3 derivatives, anthralin, tars, cytotoxic drugs and the like. The first-line drugs for topical treatment include tazarotene, corticosteroids with medium to strong effects, and calcipotriene. Physical therapies include long-wave ultraviolet (UVA) therapy, broad-spectrum UVB therapy, narrow-spectrum UVB therapy and photochemotherapy (PUVA). For refractory psoriasis such as moderate to severe psoriasis, pustule psoriasis, it is often difficult for topical treatment to produce a better therapeutic effect, while it has been confirmed that phototherapies especially PUVA have relatively good efficacy. PUVA is a method combining UVA (UVB can also be used in a small number of cases) with oral or topical psoralen (8-MOP, 5-MOP). Large amount of UVA irradiation may cause skin erythemas, burning skin, blisters and the like; and long-term use of PUVA may cause skin aging, pigmentation and skin cancers, and increase the risk of cataracts. Broad-spectrum UVB also may cause erythemas, sunburn, and pigmentation, and long-term irradiation is possibly carcinogenic. Narrow-spectrum UVB has fewer side effects such as erythemas, pigmentation, DNA damage, carcinogenicity and the like, and it has the same effectiveness as the early-stage of PUVA, but the period of remission is not long.

Photodynamic therapy (PDT) appeared in the late 1970s of the last century as a new therapeutic technique and it refers to a method which changes the function or morphology of cells of organisms or biological molecules and even causes cell damage and necrosis to achieve therapeutic effects, under the involvement of a photosensitizer and the action of light. At the beginning, PDT was mainly directed against (vascular) hyperplasic diseases, and then became one of the most active research fields in the science of tumor prevention and treatment all over the world. Recently, more and more attention has been paid to the treatment of non-tumor diseases with PDT, and for example, the non-tumor disease is genital warts, psoriasis, nevus flammeus, rheumatoid arthritis, ocular fundus macular disease, restenosis after angioplasty and the like. Currently, the PDT treatment of psoriasis is still in the research stage. Although some photosensitizer-mediated PDTs show good therapeutic effects in pre-clinical and clinical trials and in the treatment of a few cases, there is a lack of multi-central and large-scale clinical promotion around the world and there is also a lack of photosensitizer drugs used for psoriasis that acts as the main indication. The mechanism underlying the treatment of psoriasis with PDT is not fully clear yet. Existing researches indicate that it may be related to the following mechanisms: ① PDT may reduce the secretion of cytokines involved in the inflammatory mechanism, and change the secretion pattern of cytokines of monocytes in patients with psoriasis; ② PDT may inhibit the proliferation of keratinocytes; and ③ PDT may promote T cell apoptosis at skin lesions of patients with psoriasis, correct the changes in the classification of lymphocytes, especially of T lymphocytes, and regulate the immune function to some extent. As compared with PUVA, PDT uses laser as an irradiation light source, has fewer side effects for long-term application and higher safety. With the development of photosensitizers, photosensitizers used for PDT therapy of psoriasis may have a reduced toxicity as compared with early photosensitive drugs such as psoralen, on the basis of improved efficacy.

The effect of PDT largely depends on the properties of the photosensitizer, and the emergence, development and application of PDT generally get improved gradually with the development of photosensitizers. From 1900 when it was firstly found in Germany that the combination of light and a photosensitizer could produce the cytotoxic effect to April of 1993 when Ministry of Health of Canada firstly approved the clinical application of porfimer sodium all over the world, basic researches and clinical applications of PDT had gained wide attention. A photosensitizer or its metabolite is a chemical substance which may selectively gather on a target. An ideal photosensitizer should have the following characteristics: ① it has a single component, clear structure and stable property; ② it has relatively strong phototoxicity to the target cells, strong efficacy, relatively low dark toxicity and fewer side effects; ③ it has a relatively long retention time in target tissues, but does not remain or accumulate in the body permanently; ④ it has relatively high production of singlet oxygen and relatively long lifetime; ⑤ it has strong absorption in phototherapy window (600 nm~900 nm) so as to facilitate the use of a light source which may penetrate the human tissues more deeply in the treatment; and ⑥ it is soluble at physiological pH value. According to the structures and components of the photosensitizers, they may be classified into porphyrins, chlorophylls, dyes, Chinese herbal medicines and the like; according to the development time and the properties, photosensitizers may be classified into the first-, second- and third-generation photosensitizers. The first-generation photosensitizers appeared between the 1970s and the early 1980s; the main photosensitizer was a hematoporphyrin derivative (HpD); most photosensitizers were complex porphyrin mixtures with indefinite composition; their structures were controversial; they had poor absorption for red lights and poor capability of penetrating tissues; the time intervals between administration and irradiation was long; they were slowly excreted and the time for avoiding light after administration was long. Due to the above disadvantages of the first-generation photosensitizers, researches on the second-generation photosensitizers begun in the late 1980s. Improvements on the structure of porphyrin derivatives and isolation of monomer components such as benzoporphyrin derivatives (BPD), hematoporphyrin monomethyl ether (HMME) and the like were conducted firstly. Other substances studied mostly were monohydroporphines, phthalocyanines and derivatives of chlorophyll a degradation products. Phthalocyanines, coordination complexes of porphyrins, are big conjugated systems formed by 4 pyrrole units linked together via 4 N atoms. The big phthalocyanine ring can react with a metal element via complexation and may be substituted with various substituents. Phthalocyanine photosensitizers have an absorption wavelength of 600 nm to 800 nm and possess the following advantages: relatively high purity, relatively good light and heat stability as well as physiological activity, relatively strong absorption for the red light region, relatively good amphipathicity (hydrophobicity and hydrophilicity), low dark toxicity, good selectivity to tumors, relatively high molar extinction coefficients and the like. As compared with the first-generation photosensitizers, the second-generation photosensitizers have a single component, definite molecular structures, higher singlet oxygen quantum yields, fewer side effects and faster excretion in the body. Researches on the third-generation photosensitizers that are developed in recent years aim to further improve the efficacy and to reduce side effects, and attentions are paid to the applications of photosensitizers in diagnosis, dose monitoring, efficacy assessment and other aspects. As for the improvement of efficacy and reduction of side effects, the main strategy is the cross-linking with some special chemical substances on the basis of the second-generation of photosensitizers, thereby achieving the synergistic treatment by improving the selectivity for the target tissue or imparting new efficacy to the photosensitizers.

α-(8-quinolinyloxy) mono-substituted phthalocyanine zinc is a metal phthalocyanine complex, in which two structures, phthalocyanine and quinoline, are fused together, making the complex have the structural characteristics of both metal phthalocyanine and quinoline. The complex has characteristics such as definite structure and easy separation. The complex has an absorption wavelength of about 670 nm, a relatively high yield of fluorescence quantum and high oxidation stability; and the complex may be prepared into stable aqueous solution for use. Previous pharmacodynamics studies have confirmed the strong anti-tumor activity of the complex.

SUMMARY OF THE INVENTION

The present invention provides use of α-(8-quinolinyloxy) mono-substituted phthalocyanine zinc for the treatment of psoriasis, which is suitable for the treatment of psoriasis cells, animal models and patients with various types of psoriasis. α-(8-quinolinyloxy) mono-substituted phthalocyanine zinc can effectively inhibit the proliferation of HaCaT cells, inhibit the excessive proliferation of mouse vaginal epithelial cells which is induced by diethylstilbestrol and has relatively good therapeutic effect on propranolol-induced psoriasis-like lesions in guinea pig.

BRIEF DESCRIPTION OF THE DRAWINGS

FIG. 4A: Therapeutic effect of α-(8-quinolinyloxy) mono-substituted phthalocyanine zinc on propranolol-induced psoriasis-like lesions in guinea pigs (HE staining, 40×) of blank control group.

FIG. 4B: Therapeutic effect of α-(8-quinolinyloxy) mono-substituted phthalocyanine zinc on propranolol-induced psoriasis-like lesions in guinea pigs (HE staining, 40×) of model control group.

FIG. 4C: Therapeutic effect of α-(8-quinolinyloxy) mono-substituted phthalocyanine zinc on propranolol-induced psoriasis-like lesions in guinea pigs (HE staining, 40×) of irradiation without administration group.

FIG. 4D: Therapeutic effect of α-(8-quinolinyloxy) mono-substituted phthalocyanine zinc on propranolol-induced psoriasis-like lesions in guinea pigs (HE staining, 40×) of administration without irradiation group.

FIG. 4E: Therapeutic effect of α-(8-quinolinyloxy) mono-substituted phthalocyanine zinc on propranolol-induced psoriasis-like lesions in guinea pigs (HE staining, 40×) of injection administration group.

FIG. 4F: Therapeutic effect of α-(8-quinolinyloxy) mono-substituted phthalocyanine zinc on propranolol-induced psoriasis-like lesions in guinea pigs (HE staining, 40×) of topic administration group 1.

FIG. 4G: Therapeutic effect of α-(8-quinolinyloxy) mono-substituted phthalocyanine zinc on propranolol-induced psoriasis-like lesions in guinea pigs (HE staining, 40×) of topic administration group 2.

BEST MODE OF THE INVENTION

Figure 1:
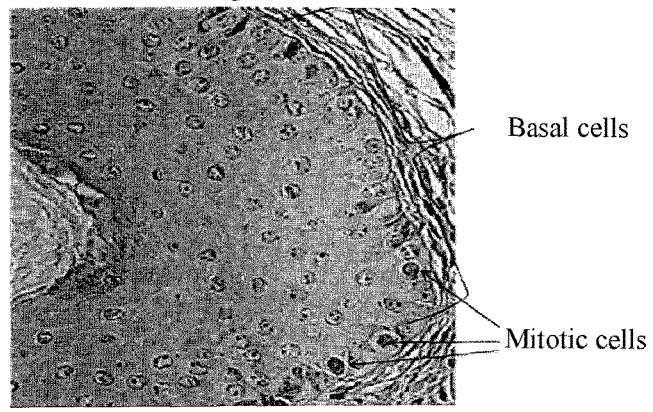
FIG. 1: Mouse vaginal epithelial basal cells and mitotic cells.

1. Effect of α-(8-quinolinyloxy) mono-substituted phthalocyanine zinc on the survival rate of HaCaT cells.

HaCaT cell line, a cell line of normally mutated and immortalized human keratinocyte, is one of the most wildly used cell models for the currently study of psoriasis. As compared with primary cultured keratinocytes, HaCaT cells have similar biological properties, but its operation is simpler.

HaCaT cells were routinely cultured in RPMI-1640 medium containing 10% fetal bovine serum at 37° C. in a 5% $CO_2$ incubator. The cells were harvested in logarithmic growth phase, digested with 0.25% trypsin (containing EDTA), adjusted to a cell density of $2 \times 10^5$ cells/mL and seeded in a 96-well plate, 100 μL per each well; after incubation for 24 hours, α-(8-quinolinyloxy) mono-substituted phthalocyanine zinc was added at concentrations of 0.001 μg/mL, 0.01 μg/mL, 0.1 μg/mL, 1 μg/mL and 10 μg/mL respectively and three complex wells were set for each concentration. A blank control group and a solvent control group were set additionally. After administration, the cells were incubated for additional 4 hours and irradiated by using a photodynamic therapeutic instrument at 670 nm. Irritation conditions: output power, 1500 mW; spot diameter, 8 cm; irradiation time, 180 s. After irradiation, the 96-well plate was placed back to the $CO_2$ incubator and incubated for additional 48 hours. The culture medium was discarded; 200 μL of MTT solution (0.5 mg/mL) was added to each well; the cells were incubated for additional 4 hours; then, 200 μL of dimethyl sulfoxide was added to each well and the absorbance value of each well was measured by a microplate reader at 545 nm (reference wavelength: 450 nm). 3 times of parallel measurements were conducted and the mean value was calculated. The inhibition rate of proliferation was calculated and IC50 was calculated by Bliss method.

Results: α-(8-quinolinyloxy) mono-substituted phthalocyanine zinc can inhibit the proliferation of HaCaT cells in a concentration-dependent manner, and under the adopted irradiation conditions, the IC50 thereof was 0.197±0.022 μg/mL.

2. Effect of α-(8-quinolinyloxy) mono-substituted phthalocyanine zinc on the diethylstilbestrol-induced excessive proliferation of mouse vaginal epithelial cells.

Estrogen (for example diethylstilbestrol) may induce the active proliferation of mouse vaginal epithelial cells, thereby accelerating the turnover of epithelial cells; and colchicine may make the cell cycle stagnated in the mitotic metaphase and then the inhibition effects of a test substance on mitosis and excessive cell proliferation may be observed. This model may simulate the characteristic of overly rapid proliferation of epithelial cells in psoriasis patients, is simple and easy to obtain, and is one of the most common animal models in the assessment of drug efficacy for psoriasis.

Sixty ICR mice were taken and randomly divided into 6 groups according to weights: blank control group, model control group, irradiation without administration group and PDT groups 1, 2 and 3. Except for the blank control group, all of other groups were intraperitoneally injected with diethylstilbestrol (0.2 mg/mouse), once-daily for 3 days. At the $4^{th}$ day, PDT groups 1, 2 and 3 were intraperitoneally injected with α-(8-quinolinyloxy) mono-substituted phthalocyanine zinc solution at doses of 1.2 mg/kg, 0.6 mg/kg and 0.3 mg/kg, respectively; and other 3 groups were not administrated. After protection from light for 6 hours, the PDT groups 1, 2 and 3 and the irradiation without administration group were subjected to laser irradiation by using a semiconductor photodynamic therapeutic instrument; the irradiation conditions were 100 mW×540 s, 300 mW×60 s, 100 mW×60 s and 300 mW×540 s, respectively; the spot diameter was 3 cm; and the abdomen of mice was irradiated. The blank control group and the model control group were not subjected to irradiation. After one week post-irradiation, mice of each group were intraperitoneally injected with colchicine at a dose of 2 mg/kg, making the cell mitosis stagnated in the mitotic metaphase. After 4 hours post-injection of colchicine, animals were sacrificed by anesthesia. Mouse vagina was taken, fixed in 10% formaldehyde solution, conventionally dehydrated, embedded in paraffin, sliced and stained with HE; 300 basal cells were counted under a microscope and the number of mitotic cells was calculated and the mitotic index was calculated (number of mitotic cells per 100 basal cells).

Figure 2:
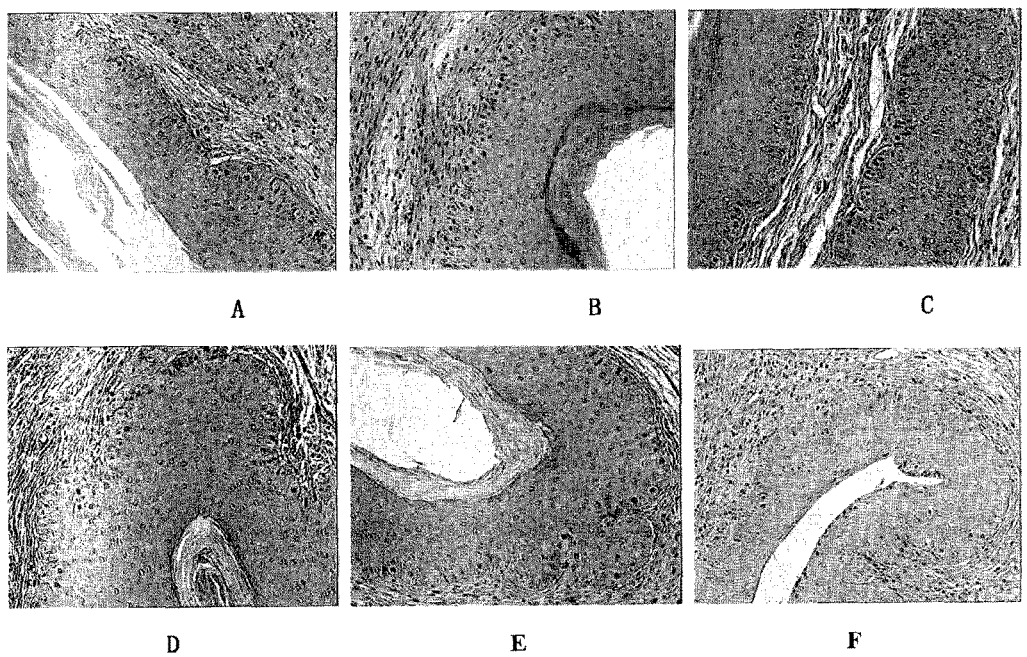
FIG. 2: Effect of α-(8-quinolinyloxy) mono-substituted phthalocyanine zinc on the diethylstilbestrol-induced excessive proliferation of mouse vaginal epithelial cells. HE staining. A, blank control group (200×); B, model control group (200×); C, irradiation without administration group (200×); D, PDT group 1 (200×); E, PDT group 2 (200×) and F, PDT group 3 (200×).

Results: diethylstilbestrol could induce the excessive proliferation of ICR mouse vaginal epithelial cells; as compared with the blank control group, the mitotic index of the model control group was increased significantly; α-(8-quinolinyloxy) mono-substituted phthalocyanine zinc-PDT could inhibit the excessive proliferation of mouse vaginal epithelial cells; as compared with the model control group, the mitotic index of PDT groups 1, 2 and 3 was significantly reduced. For details, see Table 1 and FIGS. 1-2.

TABLE 1

Effects of α-(8-quinolinyloxy) mono-substituted phthalocyanine-PDT on excessive proliferation of mouse vaginal epithelial cells ($\bar{x}$ ± s, n = 10).

| Group No. | Dose (mg/kg) | Irradiation Time (s) | Output power (mW) | Mitotic Index (%) |
|---|---|---|---|---|
| Blank control group | 0 | 0 | 0 | 5.3 ± 0.9## |
| Model control group | 0 | 0 | 0 | 19.5 ± 6.7** |
| Irradiation without administration group | 0 | 540 | 300 | 13.7 ± 5.3*## |
| PDT group 1 | 2 | 540 | 100 | 6.4 ± 2.2##^ |
| PDT group 2 | 1 | 60 | 300 | 7.2 ± 2.6## |
| PDT group 3 | 0.5 | 60 | 100 | 10.3 ± 4.3*## |

Note:
as compared with the blank control group, $*p < 0.05$, $**p < 0.01$; as compared with the model control group, $##p < 0.01$; and as compared with the irradiation without administration group, $^p < 0.05$.

3. Therapeutic effect of α-(8-quinolinyloxy) mono-substituted phthalocyanine zinc on propranolol-induced psoriasis-like lesions in guinea pig.

Propranolol is a β-adrenergic receptor blocking agent, and it may be applied to guinea pig skin to block the β-adrenergic receptor in keratinocytes and thereby reducing the intracellular cAMP level, leading to histopathological changes similar to psoriasis such as hyperkeratosis, parakeratosis and acanthosis of animal epidermis, which are the same as human psoriatic lesions at the molecular level. Application of propranolol to ear skin of guinea pig to replicate a psoriasis-like skin model is often used for observing the therapeutic effect of a drug on psoriasis.

Preparation method for 5% propranolol liniment: dissolving 5 g powder of propranolol API in 50 mL of 50% ethanol, adding 5 g of polyoxyethylene pyrrolidone 30, 2.5 mL of azone, 2.5 mL of propylene glycol, and finally adding 50% ethanol to 100 mL. 5% propranolol was prepared fresh for use. Forty-two guinea pigs were randomly divided into a blank control group and a model-establishing group according to weights, 6 guinea pigs in the blank control group and 36 guinea pigs in the model-establishing group. 5% propranolol was applied uniformly on the back of both ears of guinea pigs in the model-establishing group at a dose of 0.1 mL/ear, once in the morning and once in the afternoon, and the administration lasted for continuous 4 weeks. After the model was established, the guinea pigs in the model-establishing group were randomly divided into 6 groups according to weights again, 6 guinea pigs in each group. The 6 groups were model control group, irradiation without administration group, administration without irradiation group, injection administration group and topical administration groups 1 and 2, respectively. The administration without irradiation group and the injection administration group were intravenously injected with α-(8-quinolinyloxy) mono-substituted phthalocyanine zinc solution at a dose of 0.45 mg/kg and the topical administration groups 1 and 2 were respectively applied with 5% and 1% α-(8-quinolinyloxy) mono-substituted phthalocyanine zinc liniments at a dose of 0.1 mL/ear. Other 3 groups were not administrated. After protection from light for 24 hours, the irradiation without administration group, the injection administration group and the topical administration groups 1 and 2 were subjected to laser irradiation by using a semiconductor photodynamic therapeutic instrument with the following irradiation conditions: output power, 1,000 mW; spot diameter, 6 cm; irradiation time, 399 s; irradiation dose, 14 J/cm². After irradiation, animals were protected from light for 48 hours, and then recovered for 3 days. A photodynamic therapy (administration, irradiation, protection from light and recovery) was repeated once according to the above-mentioned steps. After the therapy, animals of each group were sacrificed by anesthesia. Skin of both sides of ear was fixed in 10% formaldehyde solution, conventionally dehydrated, embedded in paraffin, sliced and stained with HE, and observed under a microscope.

Figure 3:
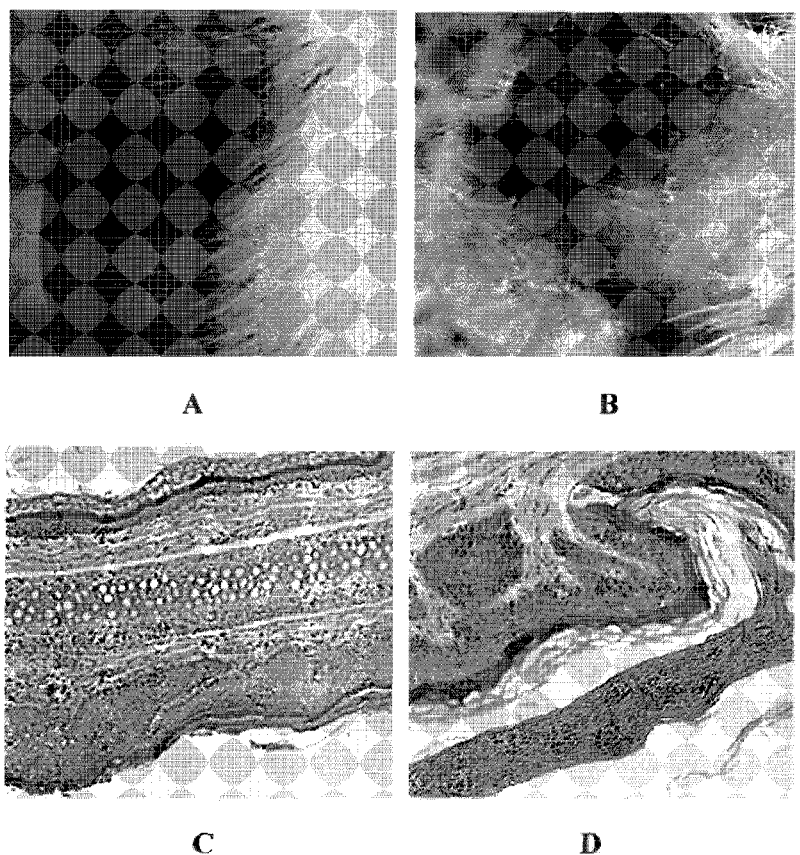
FIG. 3: Propranolol-induced psoriasis-like lesions on guinea pig ears. A, normal guinea pig ear. B, model guinea pig ear; changes such as scales, dilatation of blood vessels, thickening of skin can be observed. C, acanthosis (HE staining, 40×). D, hyperkeratosis accompanied with parakeratosis (HE staining, 200×).

Results: Application of 5% propranolol to skin on the back of ear of guinea pigs for 4 weeks can result in obvious psoriasis-like lesions; thickening of ear skin, dilatation of blood vessels and scaly lesions can be observed with naked eyes; acanthosis, hyperkeratosis and parakeratosis and the like can be observed under a microscope. For details, see FIG. 3. In the irradiation without administration group and the administration without irradiation group, such lesions got improved to some extent but not obviously. In the injection administration group and the topical administration groups 1 and 2, propranolol-induced psoriasis-like lesions of the guinea pig ear were improved significantly; after two photodynamic therapies, the prickle cell layer got thinner significantly, hyperkeratosis and parakeratosis got alleviated; some guinea pig ears were recovered to normal and had no obvious difference as compared with the blank control group. For details, see FIG. 4.

The above examples are merely the preferred examples of the present invention, and variations and modifications that are made according to the scope of the present invention come within the scope of the present invention.

What is claimed is:

1. A method of treating psoriasis in a patient, wherein the method comprises administering a photosensitizer composition comprising a zinc phthalocyanine compound of the structure:

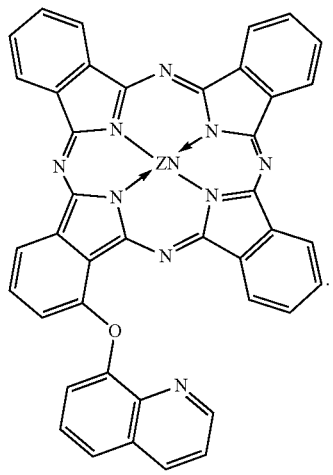

2. The method of claim 1, wherein the psoriasis is selected from the group consisting of psoriasis vulgaris, pustula psoriasis, erythrodermic psoriasis or arthritic psoriasis.

3. The method of claim 1, wherein the method of treating comprise a photodynamic therapy using a semiconductor laser with a wavelength of 670 nm as a light source.

4. The method of claim 1, wherein the composition is formulated in a form selected from the group consisting of a solution, a cream, a nanomicelle, a microsphere or a patch.

5. The method of claim 1, wherein the psoriasis is selected from the group consisting of blood heat type psoriasis, blood dryness type psoriasis, or blood stasis type psoriasis.

6. The method of claim 1, wherein the method of treatment comprises a photodynamic therapy using a semiconductor laser.

7. The method of claim 1, wherein the method of treatment comprises a photodynamic therapy using a light source.

8. The method of claim 1, wherein the mode of administration is selected from the group consisting of a systemic administration or a topical administration.

* * * * *